US009030542B2

(12) United States Patent
Hashimoto

(10) Patent No.: US 9,030,542 B2
(45) Date of Patent: May 12, 2015

(54) IMAGE PICKUP APPARATUS AND IMAGE PICKUP SYSTEM

(71) Applicant: Olympus Medical Systems Corp., Tokyo (JP)

(72) Inventor: Hidenori Hashimoto, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/914,988

(22) Filed: Jun. 11, 2013

(65) Prior Publication Data

US 2013/0329025 A1    Dec. 12, 2013

Related U.S. Application Data

(63) Continuation of application No. PCT/JP2012/083450, filed on Dec. 25, 2012.

(30) Foreign Application Priority Data

Mar. 1, 2012    (JP) .................................. 2012-045822

(51) Int. Cl.
*H04N 7/18*        (2006.01)
*A61B 1/00*        (2006.01)
(Continued)

(52) U.S. Cl.
CPC .............. *H04N 7/18* (2013.01); *A61B 1/00018* (2013.01); *A61B 1/045* (2013.01); *G02B 23/2484* (2013.01); *H04N 5/232* (2013.01); *A61B 1/00006* (2013.01); *H04N 5/3765* (2013.01)

(58) Field of Classification Search
CPC ................................................... G02B 23/2484
See application file for complete search history.

(56) References Cited

U.S. PATENT DOCUMENTS 6,976,954 B2 * 12/2005 Takahashi ...................... 600/118
2005/0018042 A1 * 1/2005 Rovegno .......................... 348/65

(Continued)

FOREIGN PATENT DOCUMENTS

EP        1 492 350 A1    12/2004
JP        2002-112958 A    4/2002

(Continued)

OTHER PUBLICATIONS

Extended Supplementary European Search Report dated Jan. 16, 2015 from related European Application No. 12 86 9817.2.

*Primary Examiner* — Andy Rao
*Assistant Examiner* — Tyler Edwards
(74) *Attorney, Agent, or Firm* — Scully, Scott, Murphy & Presser, P.C.

(57) ABSTRACT

An image pickup apparatus includes: an image pickup device for picking up an image of an object; a reception portion that is provided in a processor including a signal processing portion processes an image signal obtained by picking up the object with the image pickup device, and that receives a first synchronization signal generated in a first synchronization signal generation portion and is transmitted through a cable; a calculation portion that sequentially detects a plurality of periods of the first synchronization signal that the reception portion receives, and carries out processing to perform a calculation that determines an average value of the detected plurality of periods of the first synchronization signal; and a second synchronization signal generation portion that generates a second synchronization signal taking a value based on a calculation result of the calculation portion as a period, and supplies the second synchronization signal to the image pickup device.

4 Claims, 3 Drawing Sheets

(51) Int. Cl.
*A61B 1/045* (2006.01)
*G02B 23/24* (2006.01)
*H04N 5/232* (2006.01)
*H04N 5/376* (2011.01)

(56) References Cited

U.S. PATENT DOCUMENTS

2007/0279486 A1* 12/2007 Bayer et al. .................. 348/65
2009/0021578 A1* 1/2009 Yamazaki et al. .............. 348/65
2011/0292194 A1 12/2011 Kato

FOREIGN PATENT DOCUMENTS

| JP | 2009-045113 A | 3/2009 |
| JP | 2011-250835 A | 12/2011 |
| WO | WO 03/077560 A1 | 9/2003 |
| WO | 2007/136859 A2 | 11/2007 |

* cited by examiner

IMAGE PICKUP APPARATUS AND IMAGE PICKUP SYSTEM

CROSS REFERENCE TO RELATED APPLICATION

This application is a continuation application of PCT/JP2012/083450 filed on Dec. 25, 2012 and claims benefit of Japanese Application No. 2012-045822 filed in Japan on Mar. 1, 2012, the entire contents of which are incorporated herein by this reference.

BACKGROUND OF THE INVENTION

1. Field of the Invention

The present invention relates to an image pickup apparatus that is arranged at a distal end of an endoscope, and an image pickup system including an endoscope that includes the image pickup apparatus.

2. Description of the Related Art

Endoscopes that include an image pickup device have been widely used in medical fields and industrial fields in recent years.

Technology is also known with which an endoscope system is constructed by detachably connecting a signal processing apparatus that is referred to as a "processor" to an endoscope, and causing the processor to perform various kinds of signal processing relating to the endoscope.

With respect to such kinds of endoscope systems, a configuration is also known in which synchronization signal generation means for controlling the display of an endoscopic image is provided on a processor side, while a generation portion for generating a synchronization signal for operation of the image pickup device is arranged in a distal end portion of an endoscope insertion portion.

In the aforementioned configuration, means that generates a synchronization signal for operation of the image pickup device that is arranged in the distal end portion of the endoscope insertion portion is equipped with a function such that an external synchronization signal is inputted from a synchronization signal generation portion on the processor side and an internal synchronization signal is caused to track the external synchronization signal.

In this case, a cable that connects the synchronization signal generation means arranged in the distal end of the endoscope insertion portion and the processor extends over a comparatively long distance (see Japanese Patent Application Laid-Open Publication No. 2009-45113 as an example of transmission of a synchronization signal).

SUMMARY OF THE INVENTION

An image pickup apparatus according to one aspect of the present invention includes: an image pickup device for picking up an image of an object; a reception portion that is provided in a processor having a signal processing portion that processes an image signal that is obtained by picking up an image of the object with the image pickup device, and that receives a first synchronization signal that is generated in a first synchronization signal generation portion and is transmitted through a cable; a calculation portion that sequentially detects a plurality of periods of the first synchronization signal that the reception portion receives, and carries out processing to perform a calculation that determines an average value of the plurality of periods of the first synchronization signal that are detected; and a second synchronization signal generation portion that generates a second synchronization signal that takes a value that is based on a calculation result of the calculation portion as a period, and supplies the second synchronization signal to the image pickup device.

An image pickup system according to another aspect of the present invention includes: an image pickup apparatus having an image pickup device for picking up an image of an object; a processor that is connected through a cable to the image pickup apparatus and that has a signal processing portion that processes an image signal that is obtained by picking up an image of the object with the image pickup device; a first synchronization signal generation portion that is provided in the processor and that periodically generates a first synchronization signal; a transmission portion that is provided in the processor and that transmits the first synchronization signal to the image pickup apparatus; a reception portion that is provided in the image pickup apparatus and that receives the first synchronization signal that is transmitted from the transmission portion; a calculation portion that is provided in the image pickup apparatus and that sequentially detects periods of the first synchronization signal that the reception portion receives, and carries out processing to perform a calculation that determines an average value of a plurality of periods of the first synchronization signal that are detected; and a second synchronization signal generation portion that is provided in the image pickup apparatus and generates a second synchronization signal that takes a value that is based on a calculation result of the calculation portion as a period, and supplies the second synchronization signal to the image pickup device.

DETAILED DESCRIPTION OF THE PREFERRED EMBODIMENTS

Embodiments of the present invention are described hereunder with reference to the drawings.

First Embodiment

Figure 1:
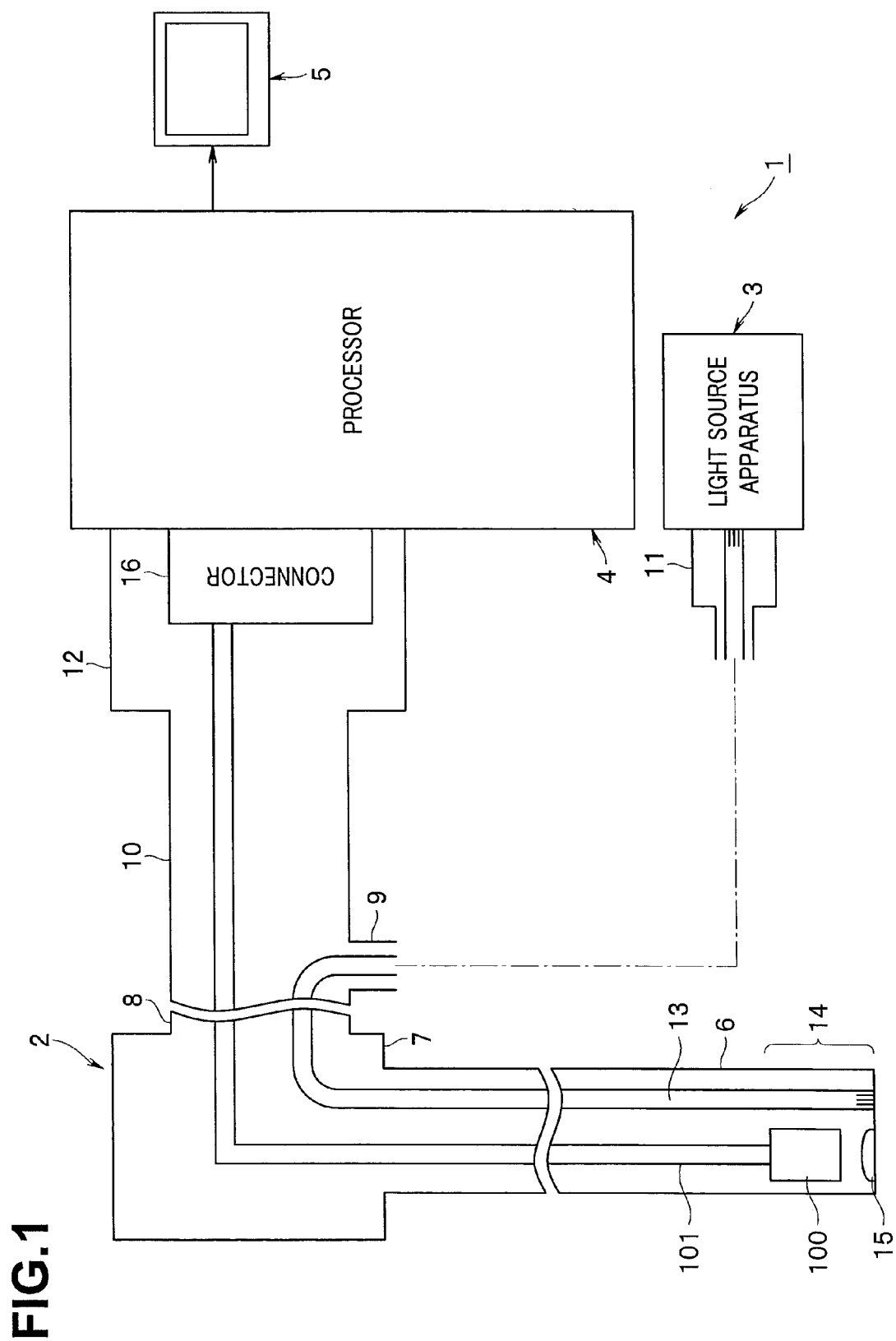
FIG. 1 is a view that illustrates the overall configuration of an image pickup system that includes an image pickup apparatus according to a first embodiment of the present invention.

As shown in FIG. 1, an image pickup system 1 including an image pickup apparatus according to a first embodiment of the present invention includes: an endoscope 2 that includes an image pickup device 100; a light source apparatus 3 that is detachably connected to the endoscope 2 and that supplies illuminating light to the endoscope 2; a processor 4 as a signal processing apparatus that is detachably connected to the endoscope 2 and carries out predetermined signal processing; and a monitor 5 as a display apparatus that displays an image signal generated by the processor 4 as an endoscopic image.

The endoscope 2 includes an elongated insertion portion 6 that is inserted into a body cavity, an operation portion 7 provided at a rear end of the insertion portion 6, and a universal cord 8 that is extended from the operation portion 7. The universal cord 8 branches into a light guide cord 9 and a signal cord (signal cable) 10 in the vicinity of the proximal end thereof or partway along the universal cord 8. A light source connector 11 at an end portion of the light guide cord 9 is detachably connected to the light source apparatus 3. A signal connector 12 at an end portion of the signal cord 10 is detachably connected to the processor 4.

A light guide 13 that transmits illuminating light is inserted through the inside of the insertion portion 6, the operation portion 7, and the universal cord 8. By connecting the light source connector 11 to the light source apparatus 3, illuminating light from the light source apparatus 3 is transmitted by the light guide 13, and the transmitted illuminating light is emitted from a light guide distal end face that is mounted in an illuminating window provided in a distal end portion 14 of the insertion portion 6. Note that a configuration may also be adopted in which a connector in which the light source connector 11 and the signal connector 12 are integrated is connected to the light source apparatus 3, and signals of the signal connector 12 are exchanged with the processor 4 by means of a cable that connects the light source apparatus 3 and the processor 4.

An observation window (image pickup window) is provided adjacent to the illuminating window in the distal end portion 14. An objective lens 15 that forms an optical image of an object such as an illuminated diseased part is mounted to the observation window. An image pickup device (hereunder, abbreviated as "CIS") 100 constituted by, for example, a CMOS image sensor, is arranged at an image-formation position of the objective lens 15.

The CIS 100 is connected to a connector 16 that is provided inside the signal connector 12 through an integrated coaxial cable 101 that is inserted through the inside of the insertion portion 6 and the universal cord 8, and the connector 16 is detachably connected to the processor 4.

The processor 4 includes: an unshown power supply circuit that generates a power supply having a plurality of different power supply voltages required for operations of the image pickup device and the like; a signal processing circuit (not shown in FIG. 1) that carries out predetermined signal processing with respect to an image pickup signal that is outputted from the image pickup device; and a control circuit (not shown in FIG. 1) that carries out control that includes control of the power supply circuit and the signal processing circuit.

Figure 2:
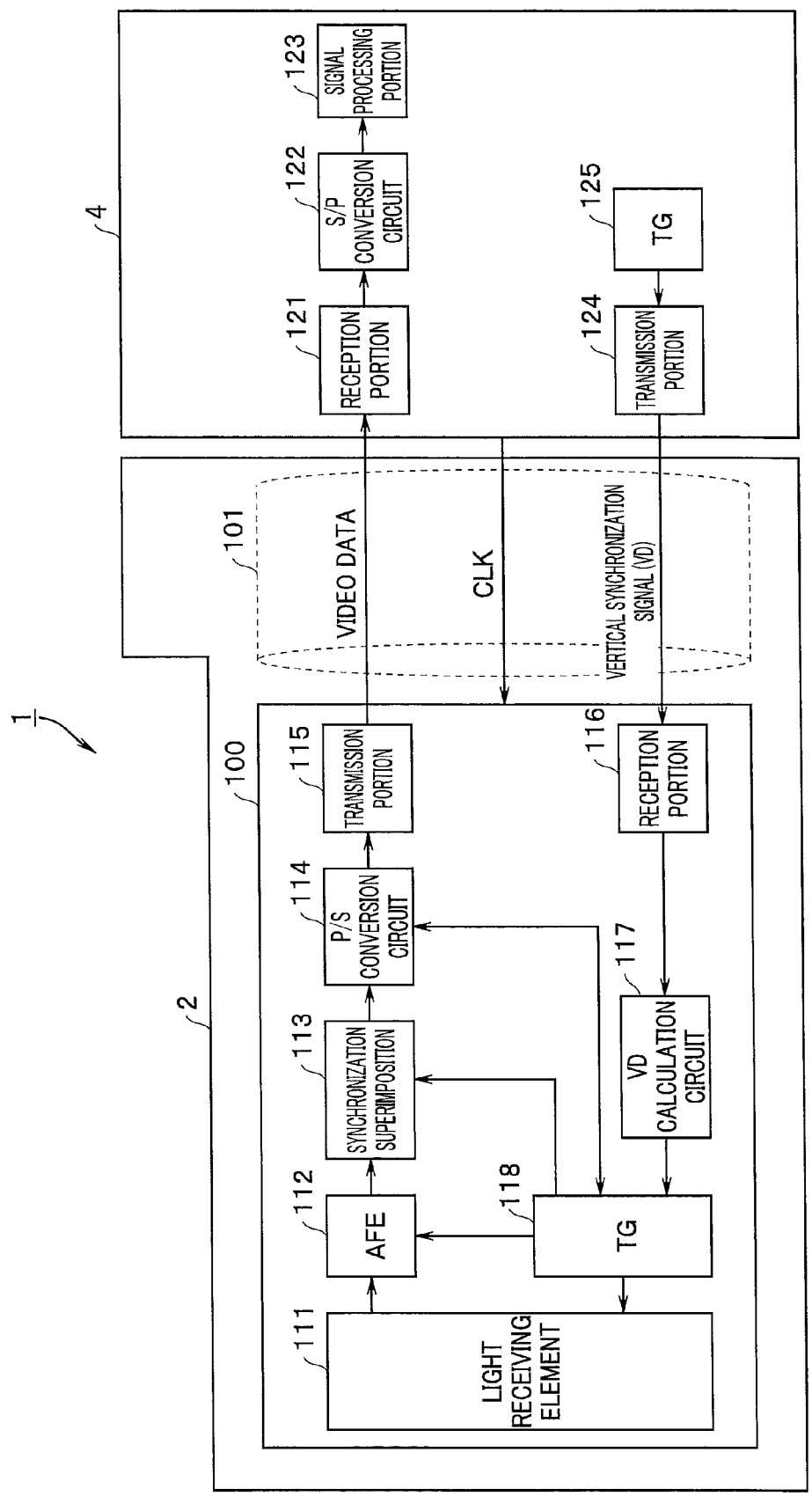
FIG. 2 is a view that illustrates the configuration of an electrical system in the image pickup system that includes the image pickup apparatus according to the first embodiment.

FIG. 2 is a block diagram that illustrates the configuration of an electrical system in an image pickup system including the image pickup apparatus according to the present embodiment.

The image pickup device (CIS) 100 according to the present embodiment is constituted by a so-called CMOS (complementary metal oxide semiconductor) image sensor, and includes: a light receiving element 111 disposed at an image-formation position of the objective lens 15; an AFE (analog front end) 112 that removes noise from a signal that was outputted from the light receiving element 111 and digitizes the signal; a synchronization superimposition circuit 113 that superimposes a synchronization signal on a video signal that is the output signal of the AFE 112; a P/S conversion circuit 114 for converting the video signal to a serial signal for transmission and outputting the resulting signal to outside; a transmission portion 115 for outputting the serial signal to outside; a reception portion 116 that receives a vertical synchronization signal (VD) and the like from, for example, the external processor 4; a VD calculation circuit 117 that performs a predetermined calculation with respect to a synchronization signal from outside (the vertical synchronization signal (VD) received from the processor 4) that the reception portion 116 receives in a predetermined case; and a timing generator (TG) 118 that generates its own synchronization signal in the CIS 100 and causes its own synchronization signal to track an external synchronization signal with respect to which a predetermined calculation was performed by the VD calculation circuit 117, and supplies its own synchronization signal to respective circuits as various synchronization signals in the CIS 100.

Note that, in the present embodiment, a synchronization signal that is generated at the timing generator (TG) 118 is taken as a first reference synchronization signal, and an external synchronization signal on which a predetermined calculation is executed by the VD calculation circuit 117 is taken as a second reference synchronization signal.

The processor 4 includes: a reception portion 121 that receives a video signal (serial signal) having video data that is transmitted from the CIS 100; an S/P conversion circuit 122 that converts a video signal (serial signal) on which a synchronization signal is superimposed that is received by the reception portion 121 to a parallel signal; a signal processing portion 123 that performs predetermined signal processing with respect to the received video signal and outputs the resulting signal to the monitor 5 or the like; a timing generator (TG) 125 that generates a vertical synchronization signal (VD) for image processing at the processor 4 and supplies the generated vertical synchronization signal (VD) to various circuits; and a transmission portion 124 that transmits the vertical synchronization signal (VD) generated in the processor 4 that is supplied from the timing generator (TG) 125, to the CIS 100.

Further, although not shown in the drawings, in addition to the above described circuits, the processor 4 also includes an unshown power supply circuit that generates a power supply having a plurality of different power supply voltages required for operations of the image pickup device and the like, and circuits such as a control circuit that carries out control of the power supply circuit and the signal processing portion and the like.

The integrated coaxial cable 101 extends from an output terminal of the CIS 100 in the insertion portion 6 and passes through the inside of the universal cord 8 and is detachably connected to the processor 4 through the connector 16 provided inside the signal connector 12.

The integrated coaxial cable 101 is a cable that connects the CIS 100 and the processor 4. Power that is supplied to the CIS 100 is transmitted through the integrated coaxial cable 101, and a video signal (serial signal) on which a synchronization signal is superimposed that is transmitted from the CIS 100 and a vertical synchronization signal (VD) that is transmitted from the processor 4 and the like are also transmitted and received through the integrated coaxial cable 101.

The integrated coaxial cable 101 is shielded by a shield member that is formed by an exterior member of the insertion portion 6. The shield member is electrically connected to a shield member formed by an exterior member of the operation portion 7, a shield member formed by an exterior member of the universal cord 8, and a shield member of the signal connector 12 and the like.

Thus, in the present embodiment, although a certain noise countermeasure is implemented in the integrated coaxial cable 101, there have been demands for increasing reductions in the diameter of endoscopes in recent years and consequently the diameters of the cables themselves have also become thinner, and as a result more advanced countermeasures are required with respect to noise.

In addition, in a case, such as in the invention of the present application, where a configuration is adopted in which the CIS 100 is disposed at a distal end of the endoscope and it is necessary to transmit a synchronization signal thereto over a comparatively long distance from the processor 4 side, measures that are more advanced than heretofore are demanded with respect to countering the intrusion of noise that is caused by disturbance.

The invention of the present application reduces the influence of the intrusion of noise that is caused by disturbance as described above by means of the solution described below.

Figure 3:
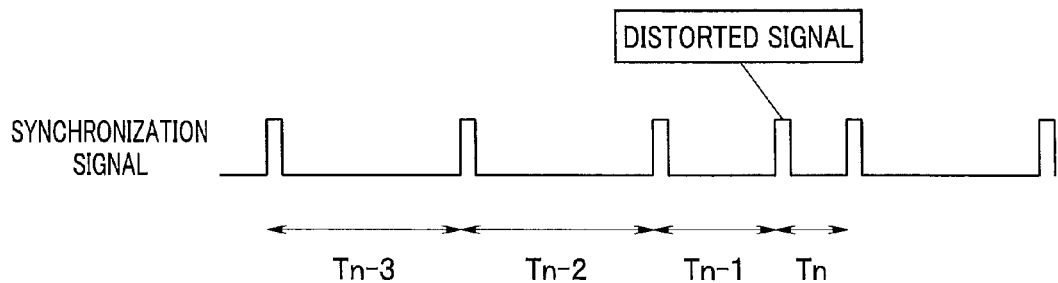
FIG. 3 is a view that illustrates an example of a synchronization signal that is distorted by disturbance according to the present invention.

FIG. 3 is a view that illustrates an example of a synchronization signal that is distorted by disturbance according to the present invention.

In the first embodiment, a vertical synchronization signal (VD) is generated at the timing generator (TG) 125 in the processor 4, and is transmitted to the CIS 100 through the integrated coaxial cable 101. As shown in FIG. 3, in this case, there is a risk that, in the vertical synchronization signal (VD) that is transmitted through the integrated coaxial cable 101, a period of a part of the synchronization signal will be distorted by the influence of noise that is caused by disturbance.

With respect to this situation, the VD calculation circuit 117 detects periods of the relevant external synchronization signal (vertical synchronization signal (VD)) that are sequentially received by the reception portion 116, and performs a calculation that applies a low-pass filter on the time axis with respect to the detected periods to determine an average value. In addition, the VD calculation circuit 117 outputs a vertical synchronization signal (VD) that is based on the determined average value to the timing generator (TG) 118 as a second reference synchronization signal.

The timing generator (TG) 118 causes the synchronization signal (first reference synchronization signal) generated by itself to track the vertical synchronization signal (VD) with respect to which the calculation was performed by the VD calculation circuit 117, and supplies the synchronization signal to various circuits.

In the present embodiment, the aforementioned average value is calculated as described hereunder.

That is, when an nth received period of a synchronization signal among k periods of the synchronization signal that are sequentially detected in the VD calculation circuit 117 is taken as a period (Tn), an average value (Tave) according to the present embodiment is determined as a moving average value, that is:

$$Tave = \Sigma(Tn-i)/k$$

where i=1 to k.

As described above, according to the image pickup system including the image pickup apparatus of the first embodiment, even when noise that is caused by disturbance mixes into the vertical synchronization signal (VD) that is transmitted from the processor side and a period of the synchronization signal is distorted, the influence of the distortion can be reduced.

Second Embodiment

Although an image pickup system including an image pickup apparatus of a second embodiment of the present invention has a similar configuration to the above described first embodiment, a calculation technique at the VD calculation circuit 117 is different from the first embodiment. Since the remaining configuration is the same as that of the first embodiment, a detailed description thereof is omitted here.

In the present embodiment, the VD calculation circuit 117 detects periods of the relevant external synchronization signal (vertical synchronization signal (VD)) that are sequentially received by the reception portion 116, and performs a calculation that determines a weighted average value with respect to the detected periods.

Thereafter, similarly to the first embodiment, the VD calculation circuit 117 outputs a vertical synchronization signal (VD) that is based on the determined average value as a second reference synchronization signal to the timing generator (TG) 118, and the timing generator (TG) 118 causes the synchronization signal (first reference synchronization signal) generated by itself to track the vertical synchronization signal (VD) with respect to which the calculation was performed by the VD calculation circuit 117, and supplies the synchronization signal to various circuits.

In the present embodiment, when determining a weighted average value, a weighting that is applied to a period (Tn) is set based on a difference value (deviation amount) between the relevant period (Tn) and the immediately preceding past average value (Tave).

Note that the stability of the average value (Tave) is increased by adjusting the weighting coefficient so as to have a negative correlation with respect to a difference value between the past average value (Tave) and the period (Tn).

In the image pickup system including the image pickup apparatus according to the second embodiment described above also, similarly to the foregoing embodiment, even when noise that is caused by disturbance mixes into the vertical synchronization signal (VD) that is transmitted from the processor side and a period of the synchronization signal is distorted, the influence of the distortion can be reduced.

Third Embodiment

Although an image pickup system including an image pickup apparatus of a third embodiment of the present invention has a similar configuration to the above described first embodiment, a calculation technique at the VD calculation circuit 117 is different from the first embodiment. Since the remaining configuration is the same as that of the first embodiment, a detailed description thereof is omitted here.

Figure 4:
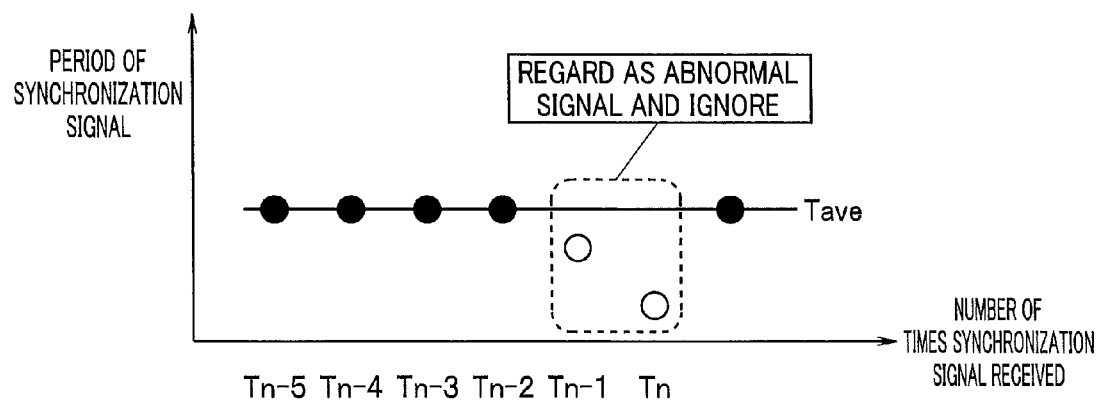
FIG. 4 is a view that illustrates an example of processing with respect to a synchronization signal that is distorted by disturbance in an image pickup system including an image pickup apparatus according to a third embodiment of the present invention.

FIG. 4 is a view that illustrates an example of processing performed with respect to a synchronization signal that is distorted by disturbance in the image pickup system including an image pickup apparatus according to the third embodiment of the present invention.

In the third embodiment, similarly to the above described first embodiment, a vertical synchronization signal (VD) is generated at the timing generator (TG) 125 of the processor 4, and the vertical synchronization signal (VD) is transmitted to the CIS 100. The VD calculation circuit 117 detects periods of the relevant external synchronization signal (vertical synchronization signal (VD)) that are sequentially received by the reception portion 116, and performs a calculation that determines an average value in a similar manner to the first embodiment by applying a low-pass filter on the time axis with respect to the detected periods.

In this case, when performing the relevant calculation, if a synchronization signal has been received in which a time difference exists that is equal to or greater than a predetermined threshold value with respect to the current average value, the VD calculation circuit 117 determines that a spurious signal that is caused by intrusion of noise due to disturbance was inputted, and ignores the calculation (excludes the calculation result) that was performed with respect to the relevant received signal, and continues with the next calculation.

Thereafter, the VD calculation circuit 117 outputs a vertical synchronization signal (VD) based on the determined average value as a second reference synchronization signal to the timing generator (TG) 118, and the timing generator (TG) 118 causes the synchronization signal (first reference synchronization signal) generated by itself to track the vertical synchronization signal (VD) with respect to which the calculation was performed by the VD calculation circuit 117, and supplies the synchronization signal to various circuits.

In the third embodiment that is described above also, similarly to the first embodiment, even when noise that is caused by disturbance mixes into the vertical synchronization signal (VD) that is transmitted from the processor side and the synchronization signal period is distorted, the influence of the distortion can be reduced.

Note that although the foregoing embodiments describe a case of an image pickup system in which means that generates a synchronization signal for image pickup control is included in a CMOS image sensor that is arranged at a distal end of an endoscope insertion portion, the present invention is not limited thereto. For example, the present invention can also be applied to an image pickup system including an endoscope in which a so-called CCD is arranged at a distal end of an endoscope insertion portion, and means that generates a synchronization signal for image pickup control is arranged in proximity to the CCD.

The present invention is not limited to the above described embodiments, and various changes and alterations can be made within a range that does not depart from the spirit and scope of the present invention, and an embodiment that is configured by partially combining the above described embodiments or the like also belongs to the present invention.

What is claimed is:

1. An image pickup apparatus connected to a second end of a cable having a first end connected to a processor and configured to be driven by an external synchronization signal supplied from the processor through the cable, the image pickup apparatus comprising:
    a light receiving element disposed at an image-formation position of an objective lens;
    a first timing generator that generates a first reference synchronization signal;
    a reception portion that receives, at the second terminal of the cable, the external synchronization signal that is transmitted from the first terminal of the cable to the second terminal of the cable through the cable, the external synchronization signal being generated in a second timing generator provided in the processor having a signal processing portion that processes an image signal outputted from the light receiving element; and
    a calculation circuit that sequentially detects a plurality of periods of the external synchronization signal that the reception portion receives, and performs a calculation that determines an average value of the plurality of periods of the external synchronization signal that are detected, to obtain a result of a calculation that eliminates influence of disturbance on the external synchronization signal partway along the transmission path through the cable, and generates a second reference synchronization signal having a value that is based on a result of the calculation as a period,
    wherein the first timing generator generates the first reference synchronization signal by causing the first reference synchronization signal to track the second reference synchronization signal; and
    the calculation circuit sequentially detects a plurality of periods of the external synchronization signal that the reception portion receives, determines a weighted average of the detected plurality of periods of the external synchronization signal, and when determining the weighted average value, changes a weighting when subjecting the plurality of periods of the external synchronization signal to weighted averaging based on a deviation amount between a period that is a calculation target of the weighted average value and an average value of the plurality of periods that is calculated immediately prior to the period that is a calculation target.

2. The image pickup apparatus according to claim 1, wherein:
    with respect to the external synchronization signal that the reception portion receives, the calculation circuit performs low-pass filtering on a time axis on the periods of the external synchronization signal to determine an average value.

3. The image pickup apparatus according to claim 1, wherein:
    in a case where a calculation result with respect to the external synchronization signal exceeds a predetermined range, the calculation circuit excludes a value that is based on the calculation result, and subsequently calculates an average value of the external synchronization signal that is next received by the reception portion.

4. An image pickup system, comprising:
    an image pickup apparatus having a light receiving element disposed at an image-formation position of an objective lens;
    a processor that is connected through a cable to the image pickup apparatus and that has a signal processing portion that processes an image signal that is obtained by picking up an image of the object with the light receiving element;
    a first timing generator that is provided in the image pickup apparatus and that generates a first reference synchronization signal;
    a second timing generator that is provided in the processor and that periodically generates an external synchronization signal;
    a transmission portion that is provided in the processor and that transmits the external synchronization signal to the image pickup apparatus;
    a reception portion that is provided in the image pickup apparatus and that receives, through the cable, the external synchronization signal that is transmitted from the transmission portion; and
    a calculation circuit that is provided in the image pickup apparatus and that sequentially detects periods of the external synchronization signal that the reception portion receives, and performs a calculation that determines an average value of a plurality of periods of the external synchronization signal that are detected, to obtain a result of a calculation that eliminates influence of disturbance on the external synchronization signal partway along the transmission path through the cable, and generate a second reference synchronization signal having a value that is based on a result of the calculation as a period,
    wherein the first timing generator supplies the first reference synchronization signal to various circuits provided in the image pickup apparatus by causing the first reference synchronization signal to track the second reference synchronization signal; and the calculation circuit sequentially detects a plurality of periods of the external synchronization signal that the reception portion receives, determines a weighted average of the detected plurality of periods of the external synchronization signal, and when determining the weighted average value, changes a weighting when subjecting the plurality of periods of the external synchronization signal to weighted averaging based on a deviation amount between a period that is a calculation target of the weighted average value and an average value of the plurality of periods that is calculated immediately prior to the period that is a calculation target.

* * * * *